(12) United States Patent
Al-Rasheed

(10) Patent No.: US 8,382,740 B2
(45) Date of Patent: Feb. 26, 2013

(54) TROCARLESS INTRAVENOUS CANNULA WITH A MULTIFILAMENT TIP

(75) Inventor: Abdullah Khalid Al-Rasheed, Riyadh (SA)

(73) Assignee: King Saud University, Riyadh (SA)

( * ) Notice: Subject to any disclaimer, the term of this patent is extended or adjusted under 35 U.S.C. 154(b) by 475 days.

(21) Appl. No.: 12/410,926

(22) Filed: Mar. 25, 2009

(65) Prior Publication Data

US 2010/0249726 A1 Sep. 30, 2010

(51) Int. Cl.
*A61M 25/00* (2006.01)
(52) U.S. Cl. ......... 604/527; 604/506; 604/523; 604/265
(58) Field of Classification Search .................. 604/506, 604/523, 96.01, 164.01, 527
See application file for complete search history.

(56) References Cited

U.S. PATENT DOCUMENTS

| 4,612,337 | A | * | 9/1986 | Fox et al. .................. 514/38 |
| 5,478,329 | A | | 12/1995 | Ternamian |
| 5,782,764 | A | * | 7/1998 | Werne .................. 600/411 |
| 6,096,012 | A | | 8/2000 | Bogert et al. |
| 2005/0038408 | A1 | * | 2/2005 | von Segesser ............. 604/506 |

* cited by examiner

*Primary Examiner* — Kevin C Sirmons
*Assistant Examiner* — Brandy C Scott
(74) *Attorney, Agent, or Firm* — Hart IP Law and Strategies

(57) ABSTRACT

A trocarless intravenous cannula with a multifilament tip is described. The trocarless intravenous cannula has a tapered, distal multifilament tip that is comprised of a plurality of individual filaments. In one aspect, the distal part of the cannula is fenestrated. The tip and the distal part of the cannula may both be covered in a dry, water-soluble coating.

7 Claims, 9 Drawing Sheets

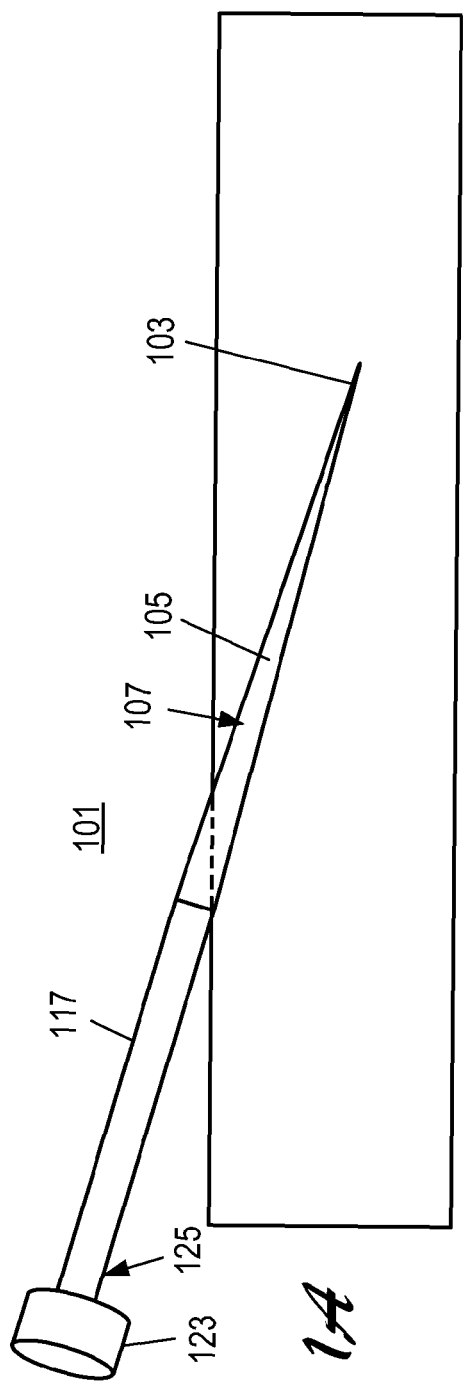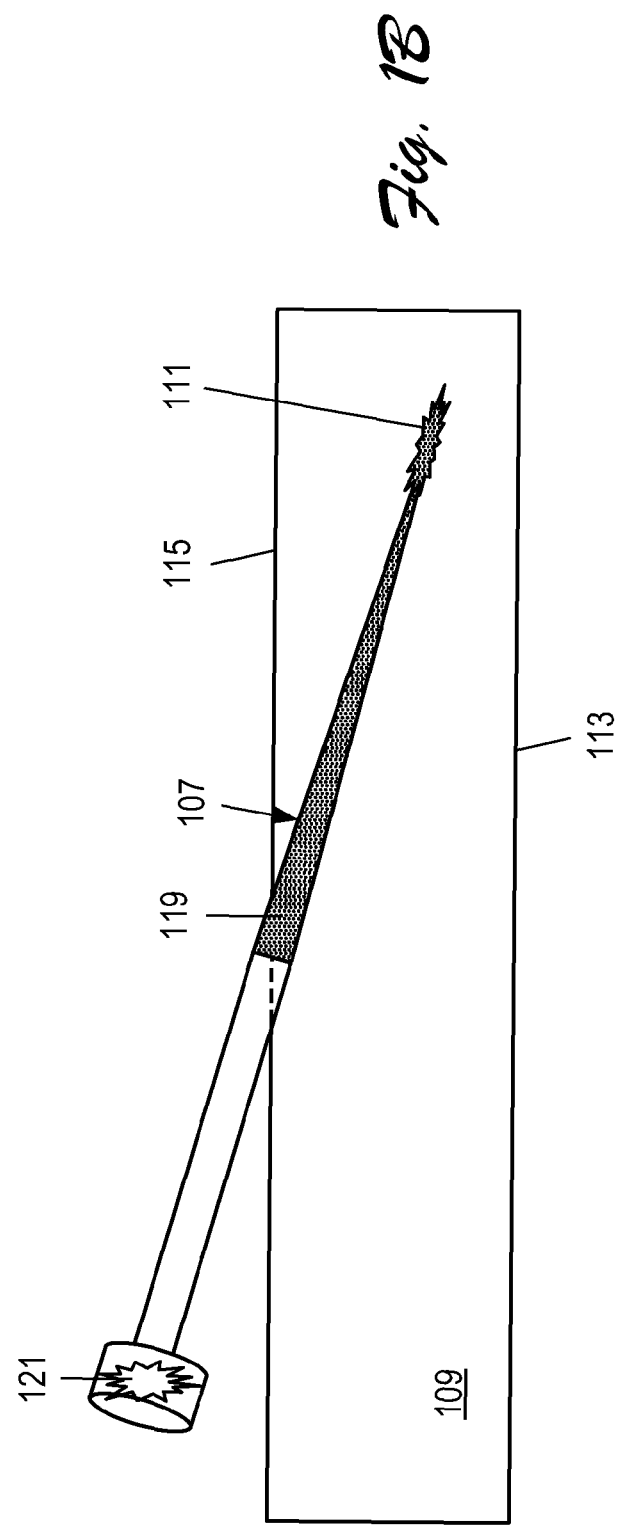

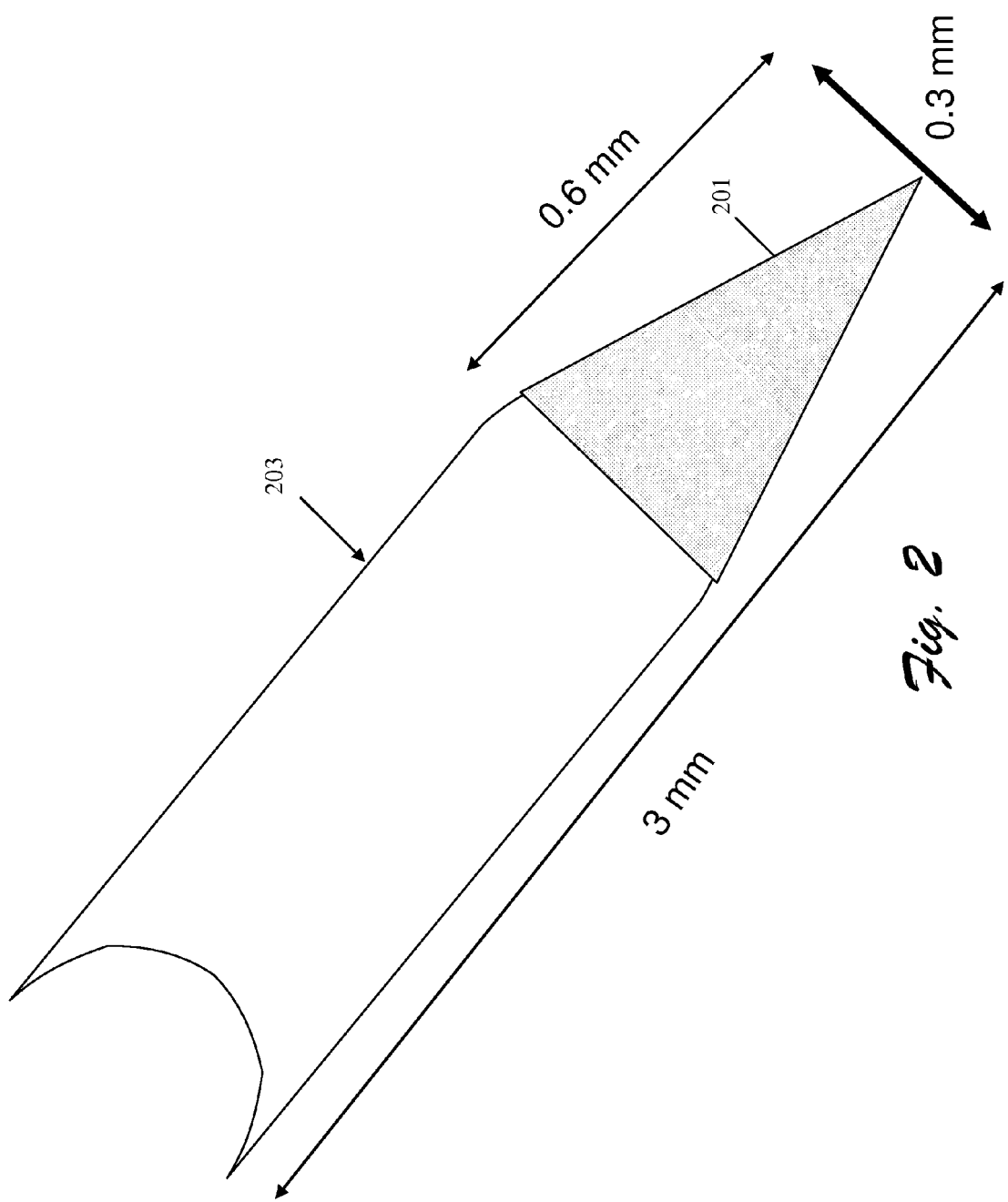

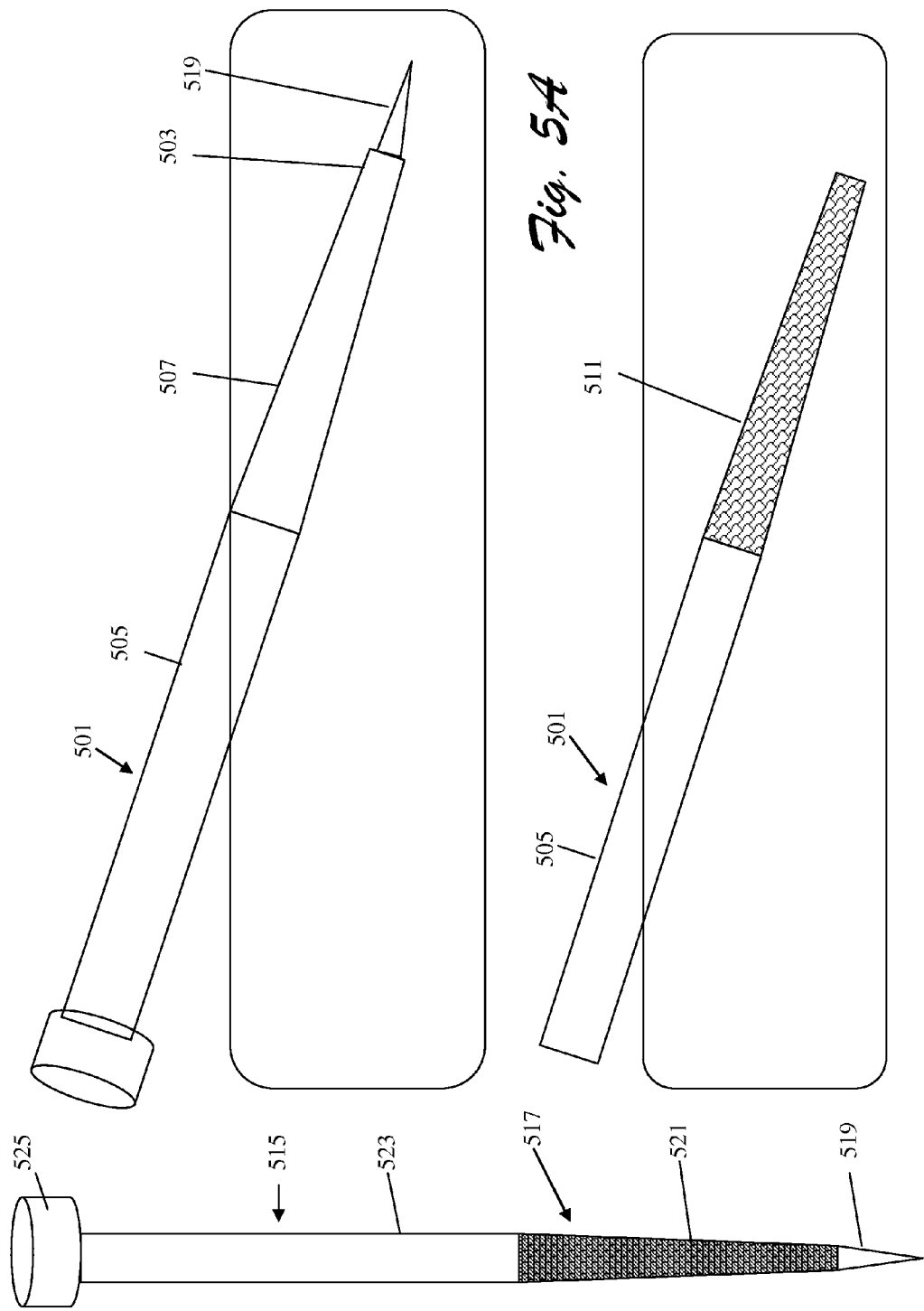

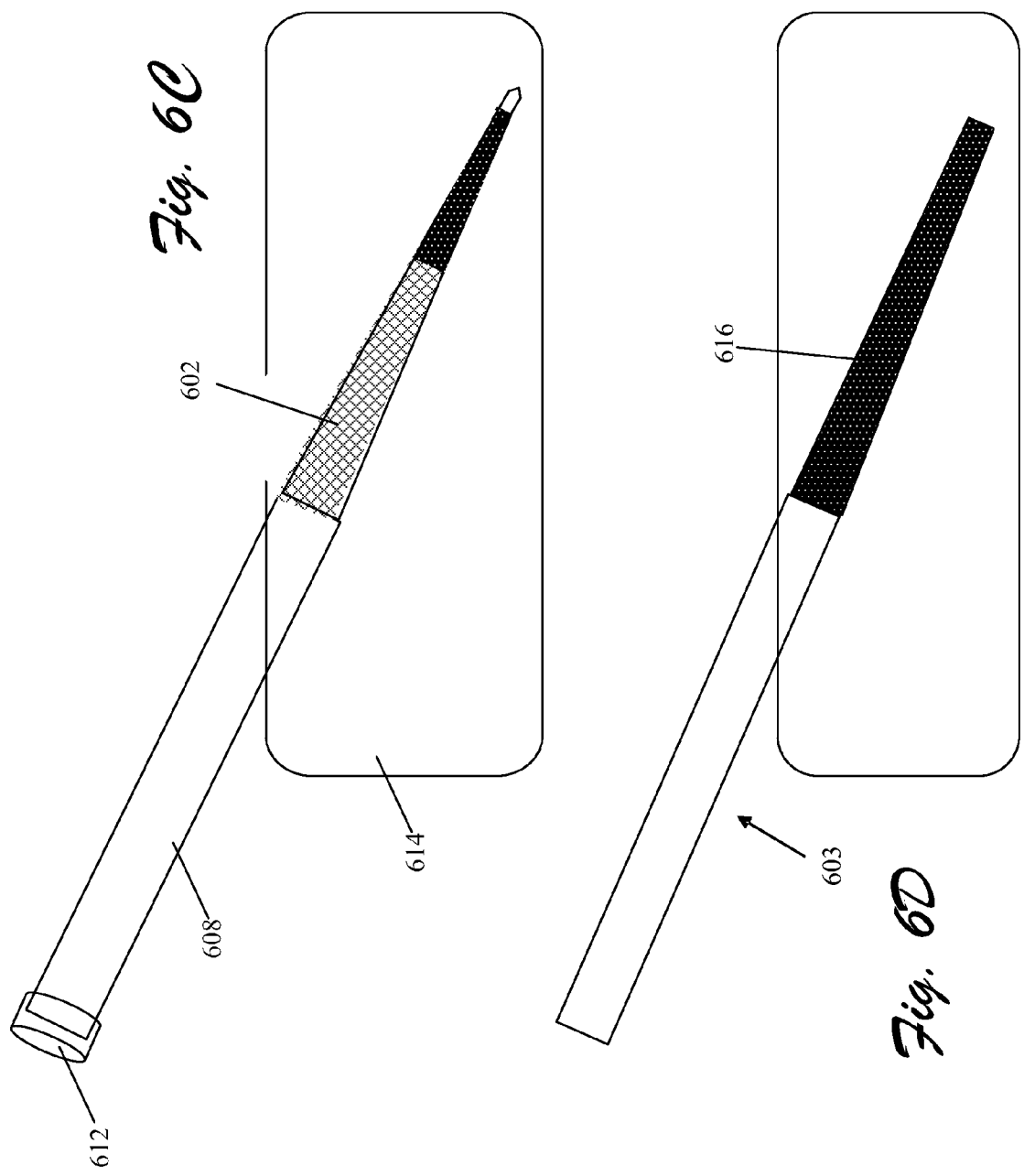

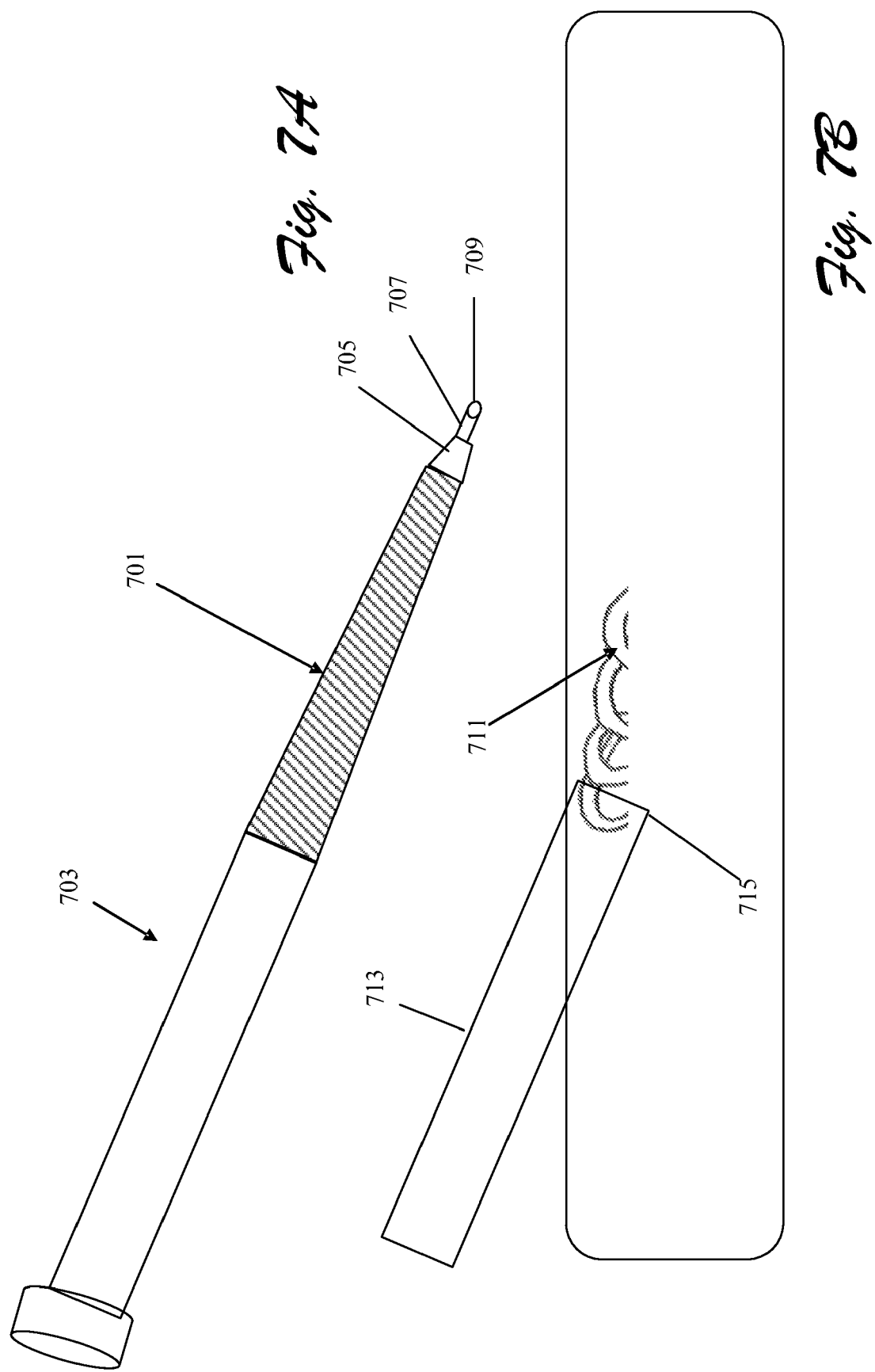

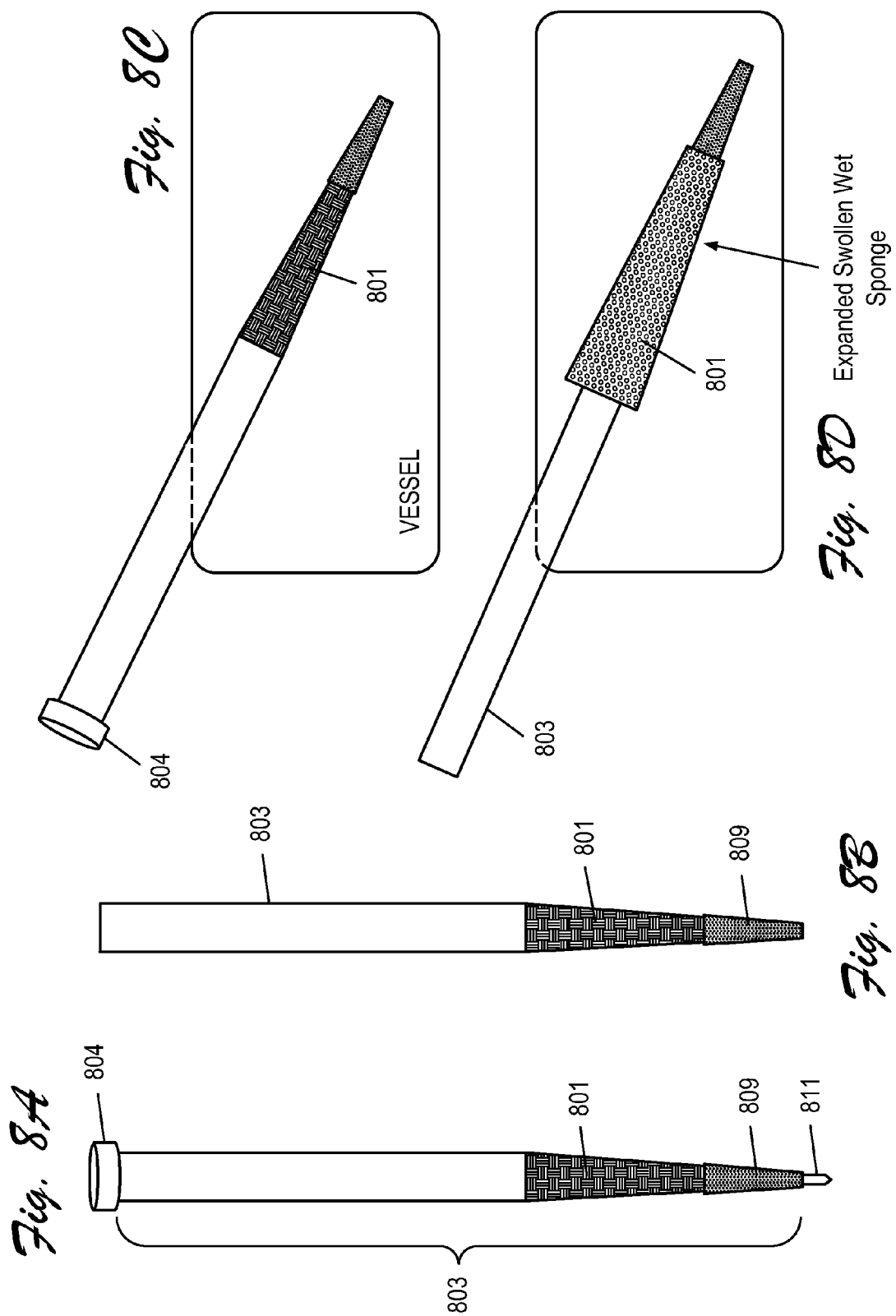

TROCARLESS INTRAVENOUS CANNULA WITH A MULTIFILAMENT TIP

BACKGROUND

A venipuncture procedure, particularly when used to insert a peripheral intravenous line in a patient, may be painful for the patient. In many instances, the procedure may have to be repeated multiple times before successful insertion of a peripheral line. Repeated probing may result in swelling or bulging veins.

Venipuncture often employs hypodermic needles. Hypodermic needles are normally made from a stainless-steel tube. The end of a hypodermic needle is typically beveled to create a sharp point at the distal tip. The sharp point at the distal tip allows the needle to easily penetrate the skin of the patient. The diameter of a hypodermic needle is indicated by a needle gauge. Various needle lengths are available for any given needle gauge. There are a number of systems for gauging needles, including the Stubs Needle Gauge and the French Catheter Scale. Needles in common medical use range from 7 gauges (the largest) to 33 gauges (the smallest) on the Stubs scale.

An intravenous cannula or catheter is a flexible tube that is generally plastic, such as polyurethane or silicon. The intravenous cannula or catheter typically has a trocar or stylet that, when inserted into the body, is used either to withdraw fluid or insert medication. Cannulae normally come with a trocar or stylet attached that punctures the body to get into the intended space. The trocar or stylet is generally removed once the cannula is in position. A small amount of blood appearing at the back of the needle signals a successful piercing of a vein. Use of a trocar or stylet may be hazardous to one's health. For example, an accidental stick needle injury may cause transmission of hepatitis, AIDS, or other hazardous condition.

A sharp distal end of the trocar is inserted inside the vein lumen with the tip of the cannula. After backflow of blood is detected, the trocar may be pulled slightly in a proximal direction and the cannula pushed slightly in a distal direction. The pulling and pushing may be repeated until the main trunk of the cannula is introduced into the vein lumen and the trocar is completely removed from the vein lumen.

SUMMARY

Systems and methods for a trocarless intravenous cannula are described. In one aspect, a trocarless intravenous cannula includes a tapered, distal multifilament tip. The tip is made of a plurality of individual filaments. The distal part of the cannula is fenestrated. In one embodiment, both the tip and the distal part of the cannula are covered in a dry water-soluble coating, ice, or other compatible material. The water-soluble material (e.g., sugar, salt, multivitamin, and/or so on) is biocompatible and biodegradable to the human body. Heparin can be infused locally, if the cannula will be locked temporarily to further time for use to prevent coagulation and clot formation due to blood stagnation (Heparin lock).

This Summary is provided to introduce a selection of concepts in a simplified form that are further described below in the detailed description. This Summary is not intended to identify key features or essential features of the claimed subject matter, nor is it intended to be used as an aid in determining the scope of the claimed subject matter.

BRIEF DESCRIPTION OF THE DRAWINGS

FIGS. 1A and 1B show an exemplary system for a trocarless intravenous cannula with a multifilament tip, according to one embodiment.

FIG. 2 is an exemplary detail of a multifilament tip in an impacted state, according to one embodiment.

FIGS. 5A-5C show an exemplary system for an intravenous cannula with a coated fenestrated tapering end, according to one embodiment.

FIGS. 6A-6D show an exemplary system for an intravenous cannula with at least a partially coated fenestrated tapering end, according to one embodiment.

FIGS. 7A and 7B show an exemplary system for an intravenous cannula with a packed coil, according to one embodiment.

FIGS. 8A-8D show an exemplary system for an intravenous cannula with a dry, compressed sponge, according to one embodiment.

DETAILED DESCRIPTION

Overview

Figure 3:
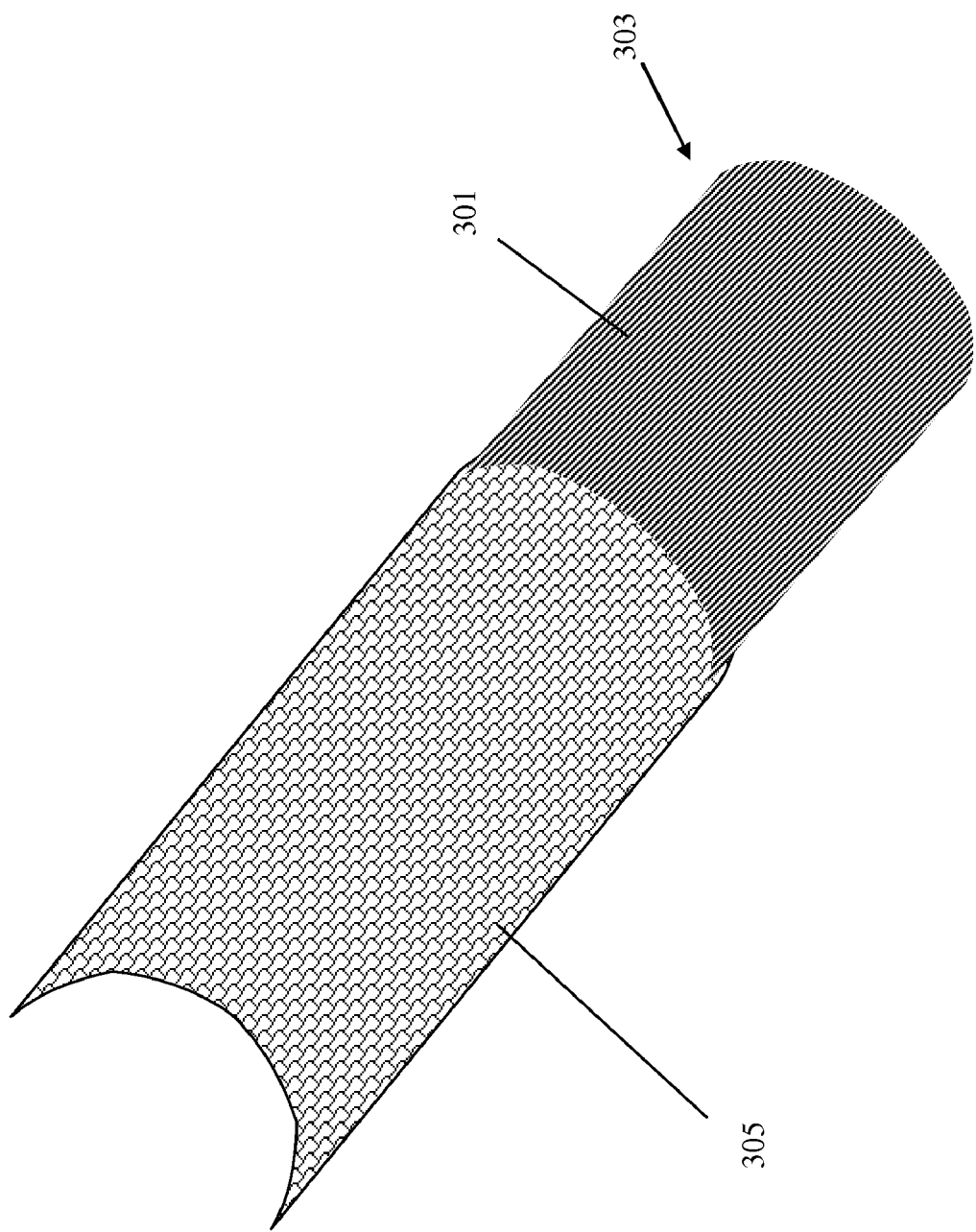
FIG. 3 is an exemplary detail of a multifilament tip in a non-impacted state, according to one embodiment.

The use of cannulae may cause vein rupture even if cannulation is successful. In children, external veins have very thin lumens and are friable. This often leads to vein puncture of the distal vessel wall with corresponding leakage of blood and extravasations of fluids. Additionally, children may generally be less likely to sit still through a procedure and/or may be severely dehydrated, resulting in collapsed veins, or hands are moving/choppy, making performance of the procedure more difficult.

Vein rupture is more common with larger sizes of cannulae. Use of a smaller size cannula may reduce some of the risk associated with vein rupture. That being said, however, even the smallest sizes of cannulae may cause vein rupture in certain circumstances. Furthermore, smaller sized cannulae may limit fluid volume for intravenous infusion because of the narrow diameter of the cannula lumen.

Systems and Methods for a Trocarless Intravenous Cannula

For intravenous cannulation, a sharp trocar or needle typically is used to pierce the skin, soft tissue, and vessel wall. FIG. 1A illustrates an exemplary embodiment of a trocarless intravenous cannula 101 with a multifilament tip 103. That is, cannula 101 does not require a trocar. The cannula 101 may be made of plastic or any other suitable material. In certain embodiments, the multifilament tip 103 of the cannula 101 is made of a plurality of impacted filaments. In exemplary embodiments, the impacted filaments are oriented parallel to a long axis of the individual filaments. Impacted filaments, which may be hundreds or more individual filaments, are oriented in a predetermined position that may be stiff and strong in tension and compression. For example, the impacted filaments may comprise carbon, graphite fiber, fiberglass, plastic, silicon, cellulose, or other suitable material such as stainless steel. All contemplated types of filaments are strong enough not to break inside the vein under normal use. An individual structural carbon fiber or glass fiber is both stiff and strong in tension and compression, i.e., along its axis. On the other hand, the carbon fiber or glass fiber is neither stiff nor strong in shear force, i.e., across its axis. Therefore, if a collection of fibers is arranged permanently in a particular direction within a material, and if the fibers are prevented from buckling in compression, then that material becomes particularly strong in that direction.

A carbon fiber is generally a long, thin strand of material about 0.005 mm to 0.010 mm in diameter and made primarily of carbon atoms. Carbon atoms may be bonded together in microscopic crystals more or less aligned parallel to a long axis of the fiber. The crystal alignment makes the fiber very strong for its size. Carbon fibers are classified by the tensile modulus of the fiber. Tensile modulus is a measure of how much pulling force a certain diameter fiber can exert without breaking. Classifications, in ascending order of tensile modulus, include "standard modulus," "intermediate modulus," "high modulus," and "ultrahigh modulus." Ultrahigh modulus carbon fibers have a tensile modulus of 72.5 million PSI to 145.0 million PSI (500 million-1.0 billion kPa). As a comparison, steel has a tensile modulus of about 29 million PSI (200 million kPa). Thus, the strongest carbon fiber is about five times stronger than steel. Carbon fiber reinforced composite materials are also considered.

Carbon fiber reinforced polymer (CFRP or CRP) is a very strong, light, and expensive composite material. CFRP is most often epoxy, but other polymers, such as polyester, vinyl ester, or nylon, are also sometimes used. Some composites contain both carbon fiber and other fibers such as Kevlar, aluminum, and fiberglass reinforcement. Graphite fiber generally refers to certain ultrahigh modulus fibers made from petroleum pitch. These fibers have an internal structure that closely approximates the three-dimensional crystal alignment characteristic of a pure form of carbon known as graphite.

Fiberglass, also typically called glass fiber, is material made from extremely fine fibers of glass. The manufacturing process for fiberglass uses large furnaces to gradually melt a sand/chemical mix to liquid form, and then extrude it through bundles of very small orifices. The small orifices are typically 17 microns to 25 microns in diameter for E-Glass and 9 microns for S-Glass. Fiberglass is used as a reinforcing agent for many polymer products; the resulting composite material, properly known as fiber-reinforced polymer (FRP) or glass-reinforced plastic (GRP), is called fiberglass in popular usage. Glass-reinforced plastic (GRP) is a composite material or fiber-reinforced plastic made of a plastic reinforced by fine fibers made of glass. Like carbon fiber reinforced plastic, the composite material is commonly referred to by the name of its reinforcing fibers (fiberglass). The plastic is thermosetting, most often polyester or vinylester, but other plastics, like epoxy (GRE), may also be used.

A resin or coating 105 of water-soluble material, ice, or other material may impact the individual filaments of the multifilament tip 103 in a predetermined position and orientation. For example, the resin or coating 105 may cover the multifilament tip 103 and a tapered, distal portion 107 of the cannula 101. In certain embodiments, the resin or coating 105 is initially in a dry state. The dry, water-soluble resin or coating 105 increases stiffness and sharpness of the multifilament tip 103. The coated, impacted filaments may create a roughly conical shape that assists in piercing of the skin, soft tissue, and vessel wall of a patient. The impacted filaments coated with dry material behave similarly to fiber reinforced plastic or polymers, i.e., the impacted filaments have increased strength in tension and compression.

Referring to FIG. 1B, in certain embodiments, once the distal portion 107 of the cannula 101 is inserted into a vessel 109, the resin or coating 105 of water-soluble material may begin to dissolve. In one embodiment, dissolution time is approximately thirty seconds, but may be shorter or longer depending on the resin or coating 105 and particular situations. For instance, the resin or coating 105 may be thin or quick-dissolving to expedite the dissolution of the resin or coating 105.

In certain embodiments, after the resin or coating 105 dissolves, at least some of the individual filaments are no longer coupled together. As a result, the multifilament tip 103 of the cannula 101 then has a brush-like end 111 made of individual filaments, as shown in FIG. 1B. The brush-like end 111 is no longer a completely impacted multifilament and, therefore, is weaker in tension and compression. Thus, the brush-like end 111 is less likely to pierce a distal wall 113 of the vessel 109, as the individual filaments may buckle when exposed to pressure against the distal wall 113 of the vessel 109. In certain embodiments, manipulation of the cannula 101 after piercing a proximal wall 115 of the vessel 109 is either clockwise or counter-clockwise with minimal forward movement along a radial axis. This movement may minimize alignment of the cylindrical axis of the individual filaments perpendicular to the distal wall 113 of the vessel 109.

Referring to FIGS. 1A and 1B, after the cannula 101 is secured in a desired position and the water-soluble resin or coating 105 dissolves, intravenous fluid may pass through the distal portion 107 and into a cannula body 117. The distal portion 107 may have a mesh or one or more fenestrations 119 below the resin or coating 105. The dissolution of the resin or coating 105 exposes the mesh or a fenestrated portion 119 (e.g., a fenestrated distal third to achieve sufficient fluid volume passage) to the vessel 109. In certain embodiments, intravenous fluid passes through the fenestrations 119. The distal portion 107 may act as a larger gauge cannula than the original tapered multifilament tip 103. The dissolution of the resin or coating 105 allows blood 121 to flow from the distal portion 107 to a hub or reservoir 123 at a proximal end 125 of the cannula 101. Verification of blood in the hub or reservoir 123 may confirm that the distal portion 107 of the cannula 101 is within the vessel 109.

The cannula 101 is less likely to perforate the distal wall 113 of the vessel 109 because the multifilament tip 103 is relatively small in length, width, and circular dimension as compared to larger gauge needles. As shown in the exemplary embodiment of FIG. 2, which shows exemplary embodiment detail of a multifilament tip in an impacted state, a tip 201 of impacted filaments is approximately 3 mm in length, while a sharp conical end 203 is approximately 0.6 mm in length. The tip 201 is approximately 0.3 mm in diameter. In other embodiments, one or more of these lengths and/or diameter is different.

FIG. 3 is an exemplary detail of a multifilament tip in a non-impacted state, according to one embodiment. Referring to FIG. 3, after insertion of the cannula, the resin or coating 105 dissolves and individual filaments 301 are no longer coupled to each other and form a brush-like tip 303. In certain embodiments, the tip 201 of impacted filaments changes from the sharp conical end 203, as shown in FIG. 2, to a cylindrical, brush-like tip 303 that may be arranged in circular or other patterns, as shown in FIG. 3. The dissolution of the resin or coating 105 may expose one or more fenestrations 305 proximal to the brush-like tip 303.

Figure 4:
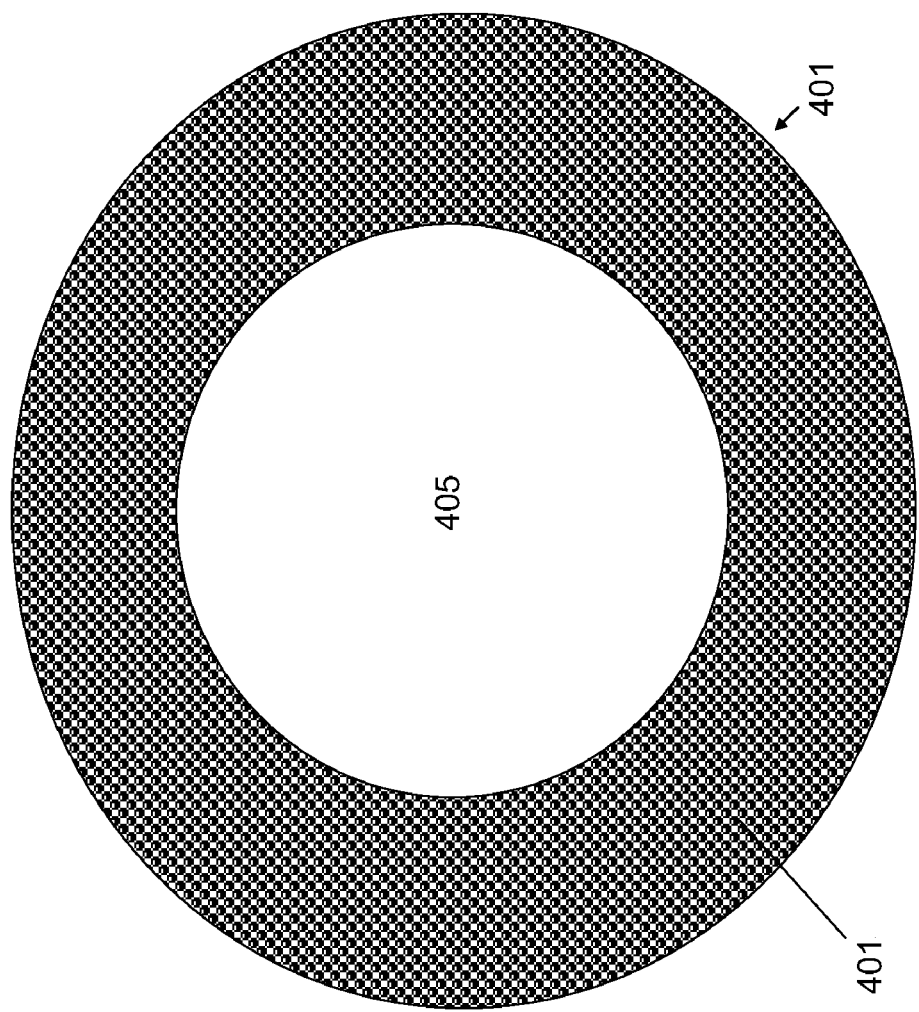
FIG. 4 is an exemplary cross-section of a multifilament tip, according to one embodiment.

FIG. 4 is an exemplary cross-section of a multifilament tip, according to one embodiment. As shown in FIG. 4, there may be hundreds or more of individual filaments 401 in a cross-section of the brush-like tip 403. In certain embodiments, the individual filaments 401 may be less than approximately 25 microns in diameter. The cannula may come in various sizes and configurations, and the number and arrangement of the multifilament may change accordingly. The individual filaments 401 may surround and/or allow access to a cannula lumen 405.

Exemplary Embodiments of Cannula with Trocar

In another embodiment, illustrated in FIGS. 5A-5C, a double gauge cannula 501 has a tip 503 that is only 33 gauge, while a trunk 505 of the cannula 501 is 21 or 23 gauge. These configurations may be referred to as 21/33 gauge and 23/33 gauge, respectively. Other sizes or configurations are possible, and these embodiments are exemplary only. In the exemplary embodiment of FIG. 5A, the cannula 501 has no hole in the tip 503. A distal section 507, which may be a quarter or a third or any other suitable amount, may be tapered to the tip 503.

As shown in FIG. 5B, a trocar 515 may also be fenestrated 521 at a distal section 517 corresponding to the distal section 507 of the cannula 501. The distal section 517 of the trocar 515 may be configured such that the distal part of the distal section 517 has a similar diameter to a trunk 523 of the trocar 515. The trocar 515 may be hollow throughout with the exception of a sharp end 519. In certain embodiments, the sharp end 519 is blind and shaped like a cone or a tip of a sewing needle. In exemplary embodiments, the distal section 517 of the trocar 515 may have one or more fenestrations 521. During cannulation, blood passes through the one or more fenestrations 521 to a cannula lumen (not shown) and then to a proximal hub or reservoir 525. As shown in the exemplary embodiment of FIG. 5C, one or more fenestrations 511 are located on the cannula 501.

Figure 6B:
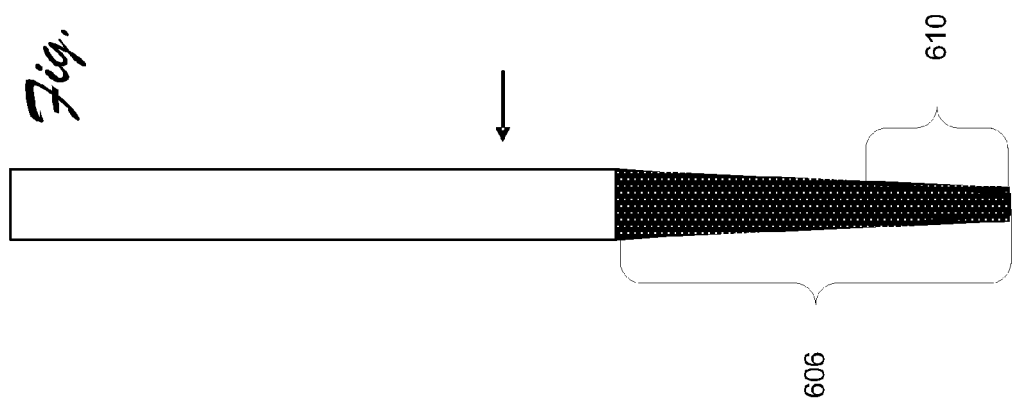
Figure 6A:
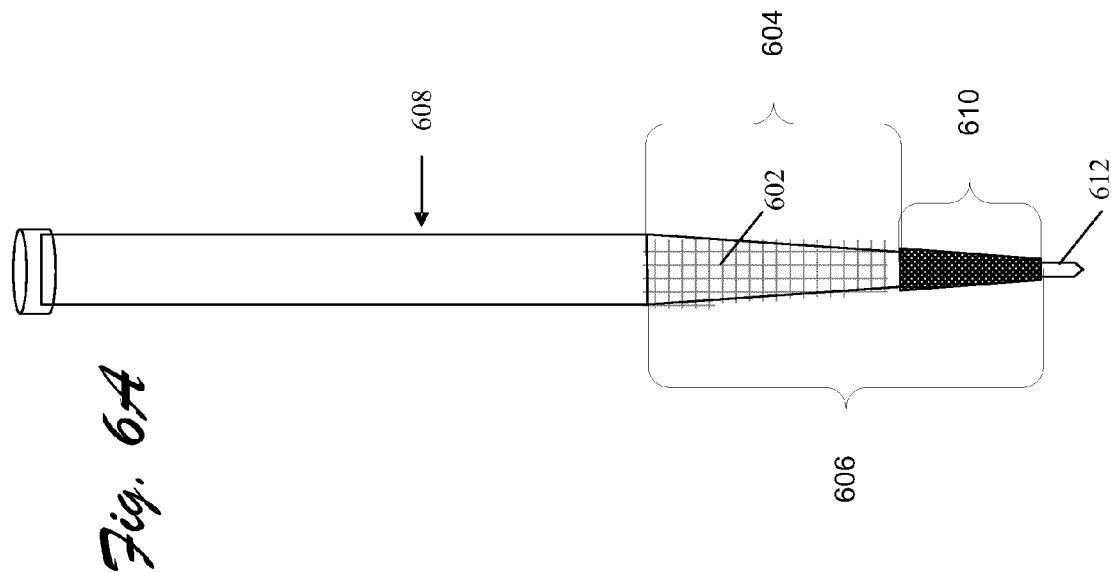

In another embodiment, illustrated in FIGS. 6A-6D, a water soluble substance may cover a portion of a cannula. As shown in FIG. 6A, a water soluble substance (e.g., salt or sugar) or frozen water (ice) coats 602 a portion 604 of a tapered area 606 of a cannula 608. Coating 602 (shown as a cross-hatch pattern) substantially conforms to the surface shape of the coated portion 604. In this embodiment, at least a portion 610 (e.g., ⅛ or some other amount) of tapered area 606 is not coated with the soluble substance. In this embodiment, there will not be any blood leakage at the top of the cannula (i.e., where the trocar cap protrudes) during insertion using trocar 612 and cannula 608. This is because the water soluble coating is not yet dissolved, or the ice has not yet melted from the patient's body temperature. This allows a number of seconds for an entity (e.g., a nurse or doctor) to fix a tube to the top of the cannula prior to blood reaching the top of the cannula device, alleviating blood leakage. A few seconds after insertion, the soluble material 602 will dissolve (or the ice will melt), and the tiny holes in the fenestrated portion of the cannula, holes that were previously inoperable due to the coating 602, will be available for use allowing the blood flow to increase. Such a scenario is shown in FIG. 6B, wherein soluble coating substance 602 (FIG. 6A) previously covering at least a portion of tapered area 604 has dissolved, revealing the fenestrations underneath. Accordingly, depending on the particular soluble substance 602 being used and other parameters such as quantity of the substance, coating 602 over the fenestrations on the cannula provide an objective way to regulate blood flow over time through the cannula.

As shown in FIG. 6C, cannula 608 with trocar 612 may be inserted into a vein 614. As shown in FIG. 6C, the coating 602 may cover at least a portion of fenestrations on the cannula. In one embodiment, the coating may cover substantially the entire fenestrated portion except a predetermined amount at the distal end of the fenestrated portion. In this scenario, the fenestration design, diameter, etc., is such that the selected soluble coating 602 will prohibit blood flow through the covered fenestrations until corresponding portions of coating 602 has dissolved. In certain embodiments, the predetermined amount is approximately the distal eighth of the cannula 603. As shown in FIG. 6D, coating 602 has dissolved, presenting substantially all of the fenestrations 616 for use (allowing blood flow into the cannula). Although the fenestrations are shown in a particular configuration and covering a certain portion of the tapered portion, other fenestration coverage and configurations are contemplated. For instance, the particular configuration and design of the fenestrations on the tapered portions can be modified according to the particular design of the cannula in view of the particular coating 602 being utilized, desired blood flow, patient comfort during insertion, etc.

FIGS. 7A and 7B show an exemplary system for an intravenous cannula and trocar with a packed coil, according to one embodiment. As shown in FIG. 7A, a packed coil 701 on a distal end of a trocar 703 is held in a compressed position by a distal band 705 made from a water-soluble material (e.g., salt, sugar, etc.), ice, other material. Such other material will comply with the described requirements to substantially block blood flow into the cannula before dissipating and allowing such blood flow. In certain embodiments, the distal band 705 may be a few millimeters in length. A trocar tip 707 may have a hole 709 at its distal end. As shown in FIG. 7B, after intravenous insertion, distal band 705 dissolves after a certain time (a function of the particular implementation of band 705), which may be several seconds, and packed coil 701 releases and expands to a resting position 711. In certain embodiments, the released coil 711 creates a cannula 713 with large gauge tip 715 for increased blood flow. Please note an original smaller size of the cannula tip as represented by the distal portion of band 705, as compared to the larger resulting diameter of cannula tip 715. In certain embodiments, trocar tip 707 may be a small gauge of 33 or thinner.

FIGS. 8A-8D show an exemplary system for an intravenous cannula with a dry, compressed sponge, according to one embodiment. FIG. 8A shows a cannula with trocar 804. FIG. 8B shows the cannula without a trocar (e.g., after the trocar has been removed). As shown in FIGS. 8A and 8B, a compressed dry sponge 801 comprises or covers at least a portion of the distal end of a cannula 807. For example, a portion of the distal end of the cannula that is not comprised of or covered by the sponge is shown as 809. There may or may not be fenestrations in area 809, as a function of the particular desired blood flow characteristics of the cannula. In one embodiment, sponge 805 is cellulose, or other similar characteristic sponge. Sponge 805 may have a thickness of approximately 50 microns, but other thicknesses may be used. A trocar tip may have a hole 811 at the distal end. Referring to FIG. 8C, after intravenous insertion, the dry sponge 805 does not allow blood to enter the cannula passageway in the usual time that it typically takes to perform a venipuncture procedure (e.g., 2 to 3 minutes). Other timeframes may be obtained by changing the types, configurations, or thicknesses of the sponges. As can be seen in FIG. 8D, after intravenous insertion, sponge 801 becomes wet and slowly expands and swells. As the sponge 801 swells, the sponge 801 becomes permeable to blood and fluids, and thereby allows blood from the punctured vein to enter the cannula passageway.

In certain embodiments, the cannula distal end has no role after insertion is completed. Even if the cannula distal end is coiled or kinked, the cannula distal end does not block the utility of the cannulae described herein. In an exemplary embodiment, the length of a cannula is longer than conventional cannulae, because of the tapered distal end. In certain embodiments, the tip of the trocar can be very thin, down to approximately 100 micrometers, acting as a micro-needle.

Although the above sections describe systems and methods for a trocarless intravenous cannula in language specific to structural features and/or methodological operations or actions, the implementations defined in the appended claims are not necessarily limited to the specific features or actions described. Rather, the specific features and operations for the trocarless intravenous cannula are disclosed as exemplary forms of implementing the claimed subject matter.

The invention claimed is:

1. A trocarless intravenous cannula comprising:

a cannula with a multifilament tip on a distal portion of the trocarless intravenous cannula, the multifilament tip being tapered to pierce skin, soft tissue, and vessel walls for cannulation of the trocarless intravenous cannula independent of a trocar, the multifilament tip comprising a plurality of individual filaments; and a water-soluble coating covering the multifilament tip, in an initial configuration, prior to dissolution of the water-soluble coating, providing the multifilament tip tapered to pierce skin;

wherein the water-soluble coating is configured to, prior to dissolution of the water-soluble coating, couple together the plurality of individual filaments of the multifilament tip with one another so as to pierce skin, soft tissue, and vessel walls; and wherein the plurality of individual filaments of the multifilament tip, in a subsequent configuration, is configured to, after dissolution of the water-soluble coating, release from one another so as to provide the multifilament tip with a brush-like end of the individual filaments.

2. The trocarless intravenous cannula of claim 1 wherein the water-soluble coating is selected from a group consisting of salt, sugar, resin, ice, or other biocompatible material.

3. The trocarless intravenous cannula of claim 1 wherein the trocarless intravenous cannula further comprises a fenestrated wall in a distal portion of the trocarless intravenous cannula.

4. The trocarless intravenous cannula of claim 3, further comprising a proximal end of the cannula with a cannula lumen, wherein the cannula lumen is in fluid communication with the one or more fenestrations.

5. The trocarless intravenous cannula of claim 3 wherein the dry, water-soluble coating covers the fenestrations on the distal end of the cannula.

6. The trocarless intravenous cannula of claim 1 wherein the plurality of individual filaments are oriented substantially parallel to a long axis of the plurality of individual filaments.

7. The trocarless intravenous cannula of claim 1 wherein the plurality of individual filaments comprise one or more of carbon, fiberglass, plastic, silicon, and cellulose.

\* \* \* \* \*